United States Patent [19]

Fischer

[11] 4,014,677
[45] Mar. 29, 1977

[54] 5-NITROPYRIMIDINE DERIVATIVES AND THEIR USE IN AGENTS FOR INFLUENCING PLANT GROWTH

[75] Inventor: Hanspeter Fischer, Bottmingen, Switzerland

[73] Assignee: Ciba-Geigy Corporation, Ardsley, N.Y.

[22] Filed: May 7, 1975

[21] Appl. No.: 575,308

[30] Foreign Application Priority Data

May 10, 1974 Switzerland .................. 6426/74

[52] U.S. Cl. .................. 71/92; 260/256.4 B; 260/256.4 C; 260/256.4 N; 260/256.5 R
[51] Int. Cl.$^2$ .................. A01N 9/22; C07D 239/30
[58] Field of Search ............ 260/256.4 N, 256.4 B, 260/256.4 C, 256.5 R; 71/92

[56] References Cited

UNITED STATES PATENTS

| | | | |
|---|---|---|---|
| 3,118,754 | 1/1964 | Nickell | 71/92 |
| 3,126,271 | 3/1964 | Thomson et al. | 71/92 |
| 3,461,461 | 8/1969 | Anthony | 260/256.5 R |
| 3,806,333 | 4/1974 | Ayad | 71/92 |
| 3,926,997 | 12/1975 | Fischer | 71/92 |
| 3,948,914 | 4/1976 | Fischer | 260/256.4 N |

OTHER PUBLICATIONS

O'Brien et al., *Journal of Medicinal Chemistry*, 9, pp. 121–126 (1966).
Brown et al., *J. Chem. Soc.*, (1965), pp. 3370–3378.

*Primary Examiner*—Paul M. Coughlan, Jr.
*Attorney, Agent, or Firm*—Harry Falber

[57] ABSTRACT

The present invention concerns new 5-nitropyrimidine derivatives and their acid addition salts as well as compositions containing them and their use, for selective pre- and post-emergent combating of weeds and for diminishing the growth of lawn, cereals and suckers. The new 5-nitropyrimidines have the formula

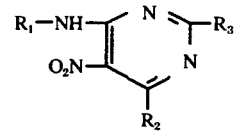

wherein $R_1$ is alkyl with 2-7 carbon atoms, alkenyl or cycloalkyl; $R_2$ is optionally substituted lower alkyl, alkoxy or alkylthio, alkenyloxy or alkenylthio, cycloalkoxy or cycloalkylthio; $R_3$ is hydrogen, lower alkyl, haloalkyl, alkoxy, alkylthio or dialkylamino.

8 Claims, No Drawings

5-NITROPYRIMIDINE DERIVATIVES AND THEIR USE IN AGENTS FOR INFLUENCING PLANT GROWTH

The present invention provides new 5-nitropyrimidine derivatives, a process for their manufacture, agents which influence plant growth which contain these pyrimidine derivatives as active substance, as well as a method of regulating plant growth which comprises the use of these active substances and agents.

Certain 4-resp.6-amino-pyrimidines are described as fungicides in French patent 1,572,620. Dutch Auslegeschrift 68.14057 cites substituted pyrimidines with fungicidal action primarily against phytopathogenic fungi on fruit and vegetable plants. Finally, DOS 2,223,644 describes 2-alkylthio-5-nitro-4,6-bis-amino-pyrimidines which regulate plant growth.

The invention is based on the surprising observation that 5-nitro-4-amino-pyrimidines of the formula I and the addition salts thereof are able to affect the plant metabolism by inhibiting the growth of grass (grass crops) and cereals as well as of suckers, e.g. of tobacco plants, without causing any appreciable damage to emergent plants as a postemergent herbicide, i.e. they have a better activity spectrum than the 5-nitro-4,6-bis-amino-pyrimidines of DOS 2,223,644.

The new 5-nitropyrimidine derivatives of the present invention have the formula I

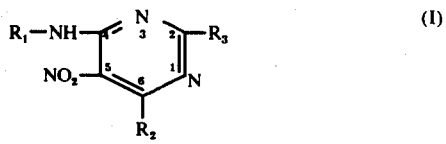

wherein $R_1$ represents an alkyl radical of 2 to 7 carbon atoms, an alkenyl or a cycloalkyl radical, $R_2$ represents an optionally substituted alkyl radical of 2 to 6 carbon atoms, an optionally substituted alkoxy or alkylthio radical of 1 to 6 carbon atoms, an alkenyloxy or alkenylthio radical of 2 to 4 carbon atoms, a cycloalkoxy or cycloalkylthio radical of 3 to 6 carbon atoms, $R_3$ represents hydrogen, an alkyl, haloalkyl, alkoxy, alkylthio or dialkylamino radical of 1 to 4 carbon atoms. Also included within the scope of the invention are the addition salts of these compounds of the formula I with inorganic and organic acids.

Particular importance attaches to those active substances according to the invention in which in formula I $R_1$ represents a preferably branched alkyl radical of 2 to 5 carbon atoms or the cyclopropyl radical, $R_2$ represents an alkyl radical of 3 to 4 carbon atoms, an alkoxy or alkylthio radical of 1 to 6 carbon atoms, the allyloxy or allylthio radical, and $R_3$ represents an alkyl, alkoxy or alkylthio radical of 1 to 4 carbon atoms or represents the trifluoromethyl radical —$CF_3$.

The most preferred pyrimidine derivatives are those of the formula I wherein $R_1$ represents the pentyl- (3) radical $C_2H_5$—CH—$C_2H_5$, $R_2$ represents an alkoxy or alkylthio radical of 1 to 4 carbon atoms and $R_3$ represents the methyl, ethyl, methylthio or the trifluoromethyl group.

By alkyl radicals in formula I are meant straightchain or branched radicals of 2 to 7 carbon atoms, e.g. ethyl, n-propyl, isopropyl, n-butyl, isobutyl, sec. butyl, tert. butyl, n-pentyl, n-hexyl, and the branched isomers of the alkyl radicals which contain 5, 6 and 7 carbon atoms. The lower, straight-chain or branched alkyl radicals also form the alkyl moiety of alkoxy, alkylthio, dialkylamino and haloalkyl groups. By alkenyl radicals $R_1$ in formula I are meant straight-chain or branched radicals of 3 to 5 carbon atoms, e.g. propenyl, butenyl, pentenyl radicals, the preferred radicals being allyl, methallyl, 3-methylbutenyl or n-butenyl. Cycloalkyl radicals $R_1$ possess 3 to 6 ring carbon atoms, e.g. cyclopropyl cyclobutyl, cyclo pentyl, cyclohexyl. The rings can be substituted by methyl or ethyl. In this specification, cycloalkyl radicals are also to be understood as meaning those radicals which can be bound through an alkyl bridge, for example the cyclopropylmethyl or cyclohexylmethyl radical.

Fluorine and chlorine are the preferred constituents of haloalkyl radicals $R_3$ and the preferred haloalkyl group is the $CF_3$ group.

If desired, alkyl, alkoxy and alkylthio radicals $R_2$ can be substituted by the following radicals: alkoxy, alkylthio, halogen and cycloalkyl.

By addition salts are meant the salts with inorganic and organic strong acids, preferably hydrochloric acid, hydrobromic acid, phosphoric acid, sulphuric acid, nitric acid, fluoroboric acid ($HBF_4$), perchloric acid, methylsulphuric or ethylsulphuric acid, halobenzoic acids, trichloroacetic acid and aromatic sulphonic acids, for example methanesulphonic acid or p-toluenesulphonic acid.

The new active substances and the agents according to the invention manufactured therewith affect the plant growth in different ways. Consequently they inhibit, delay or prevent germination but especially the growth of emergent plants, like grasses, cereals, suckers, etc. In the customary rates of application the pyrimidine derivatives of the formula I are virtually not phytotoxic to the emergent plants, but inhibit the growth in height of different plant species. If very high rates of application of more than 10 kg/hectare are used, the plants can be damaged in varying degree also after emergence and can even die. A number of active substances of the formula I also possess fungicidal, especially plant fungicidal, action.

The new active substances and agents are especially suitable for treating cereals and grass crops. The growth in height of cereals is diminished without a reduction of the crop yield being observed. For example, treatment of emergent plants of summer cereals, rye, oats, and rice (plants in the 2 leaf stage) with 0.05% dispersions of 2-methylthio-6-ethoxy-5-nitro-4-ethylaminopyrimidine effects after 21 days a 50% to 60% inhibition of the growth in height and the plants are sturdy and dark green.

Similar results are obtained with ornamental plants, e.g. Impatiens spp. and soya with 0.1% dispersions of active substance. The condition of the test plants is likewise very good. By treating existing grass crops, the growth in height of the grasses is delayed, the tillering increased. Weeds occurring in grass, for example the strongly and rapidly seeding Poa annua, dandelions, plantifinaceae, thistles etc. are very severely inhibited in their germination and emergence and virtually eliminated from existing grass crops. The inhibition of the growth in height in a mixture of grasses consisting of Poa pratensis, Festuca ovina, Festuca rubea and Lolium is between 30 and 70% (rate of application = 5 kg/hectare).

The new agents can also be used as growth regulators for decreasing the setting of fruit or for thinning out fruit clusters, for fruit abscission or delaying blossoming, as well as defoliants and for preventing undesirable sucker formation (tobacco, tomatoes, ornamental plants, vines etc.). Particular attention is drawn to the use of the active substances for inhibiting suckers in dormant tubers, for example those of ornamental plants, potatoes or onions. When applied in low rates of application, nitropyrimidines of the formula I impart to the treated plant greater resistance to drought, frost and increased salt content in the soil.

Noteworthy too is the growth inhibition and increase in yield which active substances of the formula I effect in soya plantations.

It is also possible to use the new agents as preemergent herbicides in different crops of cultivated plants, e.g. cereals, maize, rice, cotton, soya, sorghum, sugar beet, potatoes, beans, ground nuts etc. The rates of application vary and depend on the time of application. They are between 0.1 and 5 kg of active substance per hectare in preemergence application and are preferably up to 4 kg per hectare for treating existing grass crops. Normally up to 10 kg per hectare are used to prevent the growth of weeds in e.g. railway embankments, factory premises and roads.

A number of the new active substances of the formula I are suitable also for use as post-emergent herbicides, especially for combating the problem weed, Avena fatua, in cereal crops.

The pyrimidine derivatives of the formula I are obtained by processes which are known per se, namely by replacing halogen atoms in corresponding 5-nitropyrimidine derivatives which are halogenated in 4-position and optionally also in 6- or 2-position by a corresponding amino radical and, optionally, by the radical of an alcohol or mercaptan. Halogeno-5-nitropyrimidine derivatives of the formulae IIa, IIb and IIc are used as starting materials:

The nitropyrimidines of the formulae IIa, IIb and IIc are obtained by processes which are known per se by nitration of corresponding hydroxy-pyrimidines (4,6-dihydroxy-pyrimidines, 2,4,6-trihydroxy-pyrimidine and 6-hydroxy-pyrimidines) with nitric acid + glacial acetic acid/trifluoroacetic acid, nitrating mixture ($HNO_3$ + $H_2SO_4$) and subsequent introduction of halogen atoms using phosphorus halides, e.g. $POCl_3$, $PCl_5$, $PBr_5$, $PCl_3$ or with thionyl chloride or thionyl bromide. Examples of such starting materials, the majority of which are known from the literature, are: 2,4,6-trichloro-5-nitropyrimidine, 2-methylthio-4,6-dichloro-5-nitro-pyrimidine, 6-methyl-5-nitro-pyrimidine, 4,6-dichloro-5-nitro-pyrimidine, 2-methyl-4,6-dichloro-5-nitro-pyrimidine, 2-ethyl-4,6-dichloro-5-nitro-pyrimidine, 2-isopropyl-4,6-dichloro-5-nitro-pyrimidine, 2-trifluoromethyl-4,6-dichloro-5-nitro-pyrimidine, 2-n-propyl-4,6-dichloro-5-nitro-pyrimidine, 4-chloro-6-methyl-5-nitro-pyrimidine, 4-chloro-nitro-pyrimidine, 2-dimethylamino-4,6-dichloro-5-nitro-pyrimidine.

The process described herein is carried out in the presence of solvents or diluents which are inert to the reactants and of acid acceptors. The reaction temperatures are in the range of −60° to +120° C, the replacement of the first halogen atom taking place between −60° and +20° C, that of the second between 10° and 50° C or higher, and that of a possible third halogen atom between 30° and 120° C. As in generally known, such stepwise exchange reactions are dependent on temperature and solvent and, depending on the choice of these values, require reaction times from a few minutes to weeks.

Suitable solvents or diluents for the reactions according to the invention are water; ketones, such as acetone or methyl ethyl ketone; ethers and ethereal compounds, such as dioxan or tetrahydrofuran; aliphatic and aromatic hydrocarbons and halogenated hydrocarbons; also nitriles, such as acetonitrile, N,N-dialkylated amides, such as dimethyl formamide; or sulphoxides,

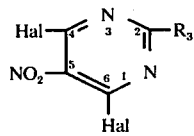
(IIa)

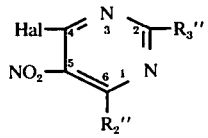
(IIb)

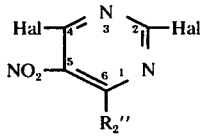
(IIc)

wherein $R_3$ has the meanings assigned to it in formula I, $R''_3$ represents alkoxy and alkylthio, $R''_2$ represents alkyl, and Hal represents halogen, especially chlorine.

To introduce the radicals of an alcohol or mercaptan into the 6-position of the starting materials of the formula IIa or into the 2-position of the starting materials of the formula IIc, there are used preferably the salts of those compounds, especially the alkali metal salts. Amines which are suitable for the exchange reaction are those of the formula III $$NH_2 - R_1 \qquad (III)$$

wherein $R_1$ has the meanings assigned to it in formula I.

If there are 2 halogen atoms in the starting material, then reaction is carried out first with the amine of the formula III and then optionally with the alcohol or mercaptan, preferably in the presence of acid acceptors.

such as dimethyl dulphoxide, as well as mixtures of these solvents.

The most suitable acid acceptors for the process according to the invention are inorganic bases, such as alkali metal and alkaline earth metal hydroxides, hydrogen carbonates and carbonates. But tertiary amines, such as trialkylamines, dialkylamines, pyridine and pyridine bases, are also suitable. A surplus of the appropriate amino component of the formula $H_2NR_1$, can also be used as acid acceptor. Preferred acid acceptors are sodium hydroxide or potassium hydroxide or a surplus of the sodium alcoholate or sodium mercaptide of the alcohol or mercaptan used.

The addition salts are manufactured by reacting the pyrimidine derivatives of the formula I in known manner with inorganic and organic acids. The strong acids, e.g. hydrohalic acids, sulphuric acid, fluoroboric acid, phosphoric acids, alkylsulphuric acids etc., are preferably used for the reaction with the pyrimidine derivatives of the formula I.

The following Examples will serve to illustrate the process according to the invention. Further pyrimidine derivatives within the scope of the formula I which were obtained in a manner analogous to that described in the Examples are subsequently listed with their physical data. Starting materials of the formulae IIa to IIc, from which the end products have been manufactured, are also tabulated.

The following Examples refer to the manufacture of the new compounds of the formula I.

EXAMPLE 1

(a) 22.5 g of ethylamine gas are bubbled into a solution of 120.1 g of 2-methylthio-4,6-dichloro-5-nitropyrimidine and 50.5 g of triethylamine in 2200 ml of absolute ethanol with cooling at −90° to −10° C. After the reaction has subsided, the mixture is evaporated to dryness and the residue is suspended in cold water, washed and isolated. Recrystallisation from hexane yields the 2-methylthio-6-chloro-5-nitro-4-ethylamino-pyrimidine of m.p. 100°–101° C.

(b) 12.5 g of 2-methylthio-6-chloro-5-nitro-4-ethylamino-pyrimidine are added to 180 ml of absolute ethanol. A solution of 4 g of sodium ethylate and 30 ml of absolute ethanol is added dropwise to this solution at 25° to 30° C while cooling slightly with ice. A precipitate falls out at room temperature after one hour. The mixture is stirred for a further 16 hours at room temperature and subsequently evaporated by rotary evaporation in a water yet vacuum. The residue is suspended in water, then filtered off with suction and washed twice with water. The filter residue is dried at 50° C over KOH (solid) at 11 mm for 16 hours. Yield: 11.9 g of 2-methylthio-6-ethoxy-5-nitro-4-ethylamino-pyrimidine of m.p. 75°–80° C. The melting point rises to 78°–81° C on recrystallisation from hexane.

EXAMPLE 2

5 g of 2-methylthio-6-chloro-5-nitro-4-ethylamino-pyrimidine are dissolved in 50 ml of absolute alcohol and 2.5 g of triethylamine are then added. Then 1 g of methylmercaptan is passed in at 25° to 30° C over a period of 10 minutes. The mixture is stirred at room temperature for ½ hour and subsequently evaporated by rotary evaporation. The residue is suspended in 50 ml of water and filtered off with suction and washed once with water. The product is dried in a water yet vacuum and at room temperature over phosphorous pentoxide for 16 hours to yield 2,6-di-methylthio-5-nitro-4-ethylamino-pyrimidine with a melting point of 149°–150° C.

EXAMPLE 3

(a) 100.0 g (0.45 mole) of 2-ethyl-4,6dichloro-5-nitro-pyrimidine are dissolved in 1 litre of ethanol and 45.5 g (0.45 mole) of triethylamine are added. 39.3 g (0.45 mole) of 3-aminopentane are added dropwise at −30° C and the mixture is stirred for 2 hours at 0° C. The reaction solution is then evaporated and the residue is suspended in 1 litre of water. Extraction is performed 3 times with ether and the ethereal extracts are dried over $MgSO_4$, filtered, and evaporated. Yield: 122 g (99.4%) of 2-ethyl-6-chloro-5-nitro-4-[pentyl-(3)-amino]-pyrimidine as an oil ($n_D^{20}$: 1.5465).

(b) 10.0 g (0.037 mole) of 2-ethyl-6-chloro-5-nitro-4-[pentyl-(3)-amino]-pyrimidine are dissolved in 100 ml of isopropanol and to this solution is added a solution of 4.34 g (0.053 mole) of sodium is isopropanol. The reaction solution is evaporated and the residue is suspended in 100 ml of water. Extraction is performed 3 times with ether and the ethereal extracts are dried over $MgSO_4$, filtered and evaporated. Yield: 3.1 g (28.6%) of 2-ethyl-6-isopropyloxy-5-nitro-4-[pentyl-(3)-amino]-pyrimidine as an oil ($n_D^{20}$: 1.55).

(c) 8.18 g (0.03 mole) of 2-ethyl-6-chloro-5nitro-4-[pentyl-(3)-amino]-pyrimidine are dissolved in 100 ml of methanol and 3.05 g (0.03 mole) of triethylamine are added to this solution. A solution of 1.45 g (0.03 mole) of methylmercaptan in 20 ml of methanol is then added dropwise and the reaction mixture is stirred for 16 hours at room temperature. The reaction solution is evaporated and the residue is suspended in 100 ml of water. Extraction is performed 3 times with ether and the ethereal extracts are dried over $MgSO_4$ filtered, and evaporated. Yield: 5.4 g (63.7%) of 2-ethyl-6-methylthio-5-nitro-4-[pentyl-(3)-amino]-pyrimidine as an oil ($n_D^{20}$:1.5665).

EXAMPLE 4

(a) 34.0 g (0.144 mole) of 2-isopropyl-4,6-dichloro-5-nitro-pyrimidine are dissolved in 500 ml of absolute ethanol and 14.6 g (0.144 mole) of triethylamine are added dropwise to this solution. Then 12.5 g (0.144 mole) of 3-aminopentane are added dropwise at −30° C and the reaction mixture is subsequently stirred for 2 hours at 0° C. The reaction solution is then evaporated and the residue is suspended in 300 ml of water. Extraction with ether is performed 3 times and the ethereal extracts are dried over $MgSO_4$, filtered, and dried. Yield: 41 g (99.3%) of 3-isopropyl-6-chloro-5-nitro-4-[pentyl-(3')-amino]-pyrimidine as an oil ($n_D^{20}$: 1.5382).

(b) 7.8 g (27 m-moles) of 2-isopropyl-6-chloro-5-nitro-4-(3-pentyl-amino)-pyrimidine are reacted with 30 m-moles of sodium ethanolate in 100 ml of ethanol. Yield: 6 g of 2-isopropyl-6-ethoxy-5-nitro-4-(3-pentylamino)-pyrimidine of m.p. 75°–80° C.

EXAMPLE 5

(a) 35.5 g (0.135 mole) of 2-trifluoromethyl-4,6-dichloro-5-nitro-pyrimidine are dissolved in 500 ml of absolute ethanol and 13.7 g (0.135 mole) of triethylamine are added to this solution. Then 11.8 g (0.135 mole) of 3-aminopentane are added dropwise at −30°C and the reaction mixture is subsequently stirred for 2 hours at 0°C. The reaction solution is then evaporated and the residue is suspended in 300 ml of water. Extraction with ether is performed 3 times and the ethereal extracts are dried over $MgSO_4$, filtered and evaporated. Yield: 44.2 g (99.5%) of 2-trifluoromethyl-6-chloro-5-nitro-4-[pentyl-(3)-amino]-pyrimidine as an oil ($n_D^{20}$: 1.5014).

(b) 4 g (13 m-moles) of 2-trifluoromethyl-6-chloro-5-nitro-4-pentyl-(3)-aminopyrimidine are reacted with 1.3 g (13 m-moles) of triethylamine and 1 g (13 m-moles) of isopropylmercaptan in 100 ml of ethanol. Yield: 4 g of 2-trifluoromethyl-6-isopropylthio-5-nitro-4-pentyl-(3)-amino-pyrimidine of m.p. 47°–50° C.

EXAMPLE 6

(Intermediate)

5.25 g (0.02 mole) of 4,6-dichloro-5-nitro-2-trifluoromethyl-pyrimidine are dissolved in 100 ml of absolute ethanol and the solution is cooled to −30° C. At this temperature 2.0 g (0.02 mole) of triethylamine as acid acceptor and 0.9 g (0.02 mole) of ethylamine are added. The mixture is stirred initially for 4 hours at −20° to −30° C and then for 6 hours at 0° C. After it has been left to stand overnight at 20° C, the reaction mixture is concentrated to dryness and the residue is taken up in water and washed with water. The ethereal phase is dried and concentrated to yield 5.3 g of 4-ethylamino-6-chloro-5-nitro-2-trifluoromethyl-pyrimidine as a pale yellow oil ($n_D^{20}$: 1.4985).

EXAMPLE 7

(a) 15 g (0.0675 mole) of 2-ethyl-4,6-dichloro-5-nitro-pyrimidine are dissolved in 300 ml of absolute ethanol and the resultant solution is treated at −30° C with 6.9 g (0.0675 mole) of triethylamine and 3.4 g (0.0675 mole) of ethylamine. The reaction mixture is stirred initially for 4 hours at −25° C and then for 6 hours at 0° to −10° C. After it has been left to stand overnight, the reaction mixture is concentrated to dryness. The product is taken up in water and extracted with ether. Yield: 17 g of 2-ethyl-4-ethylamino-6-chloro-5-nitro-pyrimidine of m.p. 35° C.

(b) 11.5 g (50 m-moles) of 2-ethyl-4-ethylamino-6-chloro-5-nitro-pyrimidine are reacted with 55 m-moles of sodium-(3)-pentanolate in 3-pentyl alcohol in analogous manner to Example 1 (b) to yield 5 g of 2-ethyl-4-ethylamine-6-(3-pentyloxy)-5-nitro-pyrimidine as an oil ($n_D^{20}$: 1.5359).

EXAMPLE 8

(a) 93.5 g (0.45 mole) of 2-methyl-4,6-dichloro-5-nitro-pyrimidine are dissolved in 1 liter of ethanol and 60 ml of triethylamine are added to this solution. Then 43.5 g of 3-aminopentane are added dropwise at 20° C and the reaction mixture is subsequently stirred for 1 hour at −1° C to −5° C. The mixture is drowned into c. 1 liter of water and extraction with ether is performed 3 times. The ethereal extracts are dried over MgSO₄ and evaporated to yield 93 g of crude product. This product is distilled at 0.1 Torr and 117°–120° C. The yield is 61.1 g (= 52%) of 2-methyl-6-chloro-5-nitro-4-[pentyl-(3')-amino]-pyrimidine of m.p. 41°–43° C.

(b) 12.9 g of 2-methyl-4-chloro-5-nitro-6-(3-pentylamino)-pyrimidine (0.05 mole) are reacted in dimethyl sulphoxide (c. 100 ml) with 4.0 g of sodium cyclopropanolate (0.05 mole) to yield 2-methyl-4-cyclopropoxy-5-nitro-6-(3-pentylamino)-pyrimidine.

EXAMPLE 9

(a) 111 g (0.5 mole) of 2-ethyl-4,6-dichloro-5-nitro-pyrimidine are reacted with 59.1 g (1.0 mole) of isopropylamine. To yield 97 g of 2-ethyl-6-isopropylamino-5-nitro-4-chloro-pyrimidine of m.p. 51°–52° C.

(b) 5.6 g (75 m-moles) of allylmercaptan and 7.6 g (75 m-moles) of triethylamine are added to 12.1 g (50 m-moles) of 2-ethyl-4-chloro-5-6-isopropylamino-pyrimidine in 100 ml of ethanol and the mixture is stirred overnight at 20° C. After the reaction mixture has been evaporated, the residue is suspended in ether and extracted with ether. The ethereal extracts are dried over MgSO₄ and evaporated to yield 12 g of 2-ethyl-4-allylthio-5-nitro-6-isopropylamino-pyrimidine as an oil ($n_D^{20}$: 1.5945).

EXAMPLE 10

12.1 g (50 m-moles) of 2-ethyl-4-chloro-5-nitro-6-isoproplamino-pyrimidine (vide Ex. 9a) are reacted with a solution of 50 m-moles of sodium cyclopentanolate is cyclopentyl alcohol to yield 8.8 g of 2-ethyl-4-cyclopentyloxy-5-nitro-6 -isopropylamino-pyrimidine as a yellow oil ($n_D^{20}$: 1.5432).

EXAMPLE 11

12.1 g (50 m-moles) of 2-ethyl-4-chloro-5-nitro-6-isopropylamino-pyrimidine (vide Ex. 9a) are reacted with 7.0 g (60 m-moles) of cyclohexylmercaptan and 6.1 g (60 m-moles) of triethylamine to yield 12.0 g of 2-ethyl-4-cyclohexylthio-5-nitro-6-isopropylamino-pyrimidine of m.p. 69°–71° C.

EXAMPLE 12

20.1 g of 2-methylthio-4-chloro-5-nitro-6-(3-pentylamino)-pyrimidine (0.069 mole) are dissolved in 450 ml of alcohol and a solution of 4.9 g of sodium (0.212 mole) in 150 ml of alcohol is added. The reaction mixture is stirred for 2 horus at 50° C and subsequently overnight at room temperature and then evaporated. The residue is treated with c. 500 ml of water and extraction is performed 3times with ether. The ethereal extracts are dried over magnesium sulphate and evaporated. The resultant oil (5.4 g) is distilled in a high vacuum to yield 2.1 g (= 10%) of 2,4-bis-ethoxy-5-nitro-6-(3-pentylamino)-pyrimidine of m.p. 38°–40° c.

EXAMPLE 13

(a) 200 ml of alcohol and 4.5 g (44 m-moles) of triethylamine are added to 11 g (44 m-moles) of 2-n-butyl-4,6-dichloro-5-nitro-pyrimidine. At −50° C, 4.0 g (44 m-moles of 3-aminopentane are added dropwise. The reaction mixture is stirred for 3 hours and then evaporated. The residue is suspended in 100 ml of water and extraction is performed with ether. The ethereal extracts are dried over MgSO₄ and evaporated to yield 10.5 g of 2-n-butyl-4-chloro-5-nitro-6-(3-pentylamino)-pyrimidine ($n_D^{20}$: 1.5383) as a yellow oil (b) A solution of sodium ethylate in ethanol, prepared from 0.15 g of sodium (7 m-moles) in 20 ml of ethanol, is added dropwise to 1.5 g (3 m-moles) of 2-n-butyl-4-chloro-5-nitro-6-(3-pentylamino)-pyrimidine in 50 ml of ethanol. The reaction solution is stirred for 3 hours and then evaporated. The residue is purified by adsorption chromatography on silica gel by elution with benzene. Yield: 1 g of 2-n-butyl-4-ethoxy-5-nitro-6-(3-pentylamino)-pyrimidine ($n_D^{20}$: 1.5310) as a yellow, semi-crystalline oil.

EXAMPLE 14

(a) 28.6 g (0.5 mole) of cyclopropylamine are added dropwise ar −50° C to 55.5 g (0.25 mole) of 2-ethyl-4,6-dichloro-5-nitro-pyrimidine in 1 liter of ethanol. The rection mixture is stirred for 3 hours at room temperature and then cooled to −40° C. The crystalline precipitate that has formed is filtered off and dried. Yield: 21 g of 2-ethyl-4-chloro-5-nitro-6-cyclopropylamino-pyrimidine of m.p. 61°–62° C. A Further 22 g of 2-ethyl-4-chloro-5-nitro-6-cyclopropylamino-pyrimidine of m.p. 61°–62° C are obtained by evaporating the filtrate, suspending the residue in water, extracting with ether, drying the ethereal extracts over MgSO₄ and evaporating them.

(b) A solution of sodium ethylate in ethanol, prepared from 1.2 g of sodium (50 m-moles) in 50 ml of ethanol, is added to 12.1 g (50 m-moles) of 2-ethyl-4-chloro-5-nitro-6-cyclopropylamino-pyrimidine in 100 ml of ethanol. The reaction mixture is stirred for 3 hours and the ethanol is subsequently evaporated off. The residue is purified by adsorption chromatography on silica gel by elution with benzene. Yield: 8 g of 2-ethyl-4-ethoxy-5-nitro-6-cyclopropylamino-pyrimidine of m.p. 79°–80° C.

EXAMPLE 15

12.1 g (50 m-moles) of 2-ethyl-4-chloro-5-nitro-6-cyclo-propylamino-pyrimidine (vide Ex. 14 a) are reacted with 50 m-moles of 2-methoxy-ethanolate in 100 ml of ethylene glycol monomethyl ether. Yield: 7 g of 2-ethyl-4-(2-methoxy)-ethoxy-5-nitro-6-cyclo-propylamino-pyrimidine as an oil ($n_D^{20}$: 1.5572).

EXAMPLE 16

(a) 28.6 g (0.5 mole) of allylamine are added dropwise at −50° C to a solution of 55.5 g (0.25mole) of 2-ethyl-4,6-dichloro-5-nitro-pyrimidine in 1 liter of ethanol. The reaction mixture is stirred overnight at 20° C and the ethanol is then distilled off. The oily residue is stirred in ice water whereupon the product crystallises. After it has been filtered off, the residue is taken up in ether, dired over MgSO$_4$, concentrated, and the residual oil is crystallised from petroleum ether by cooling. Yield: 46 g of 2-ethyl-4-chloro-5-nitro-6-allylamino-pyrimidine of m.p. 30°–32° C.

(b) 5 g (50 m-moles) of triethylamine and 4.5 g (75 m-moles) of ethyl mercaptan are added to 12.1 g (50 m-moles of 2-ethyl-4-chloro-5-nitro-6-allylamino-pyrimidine in 50 ml of ethanol. Afther the batch has been stirred overnight at 20° C, the reaction product which has crystallised out is filtered off and dried. Yield: 11 g of 2-ethyl-4-ethylthio-5-nitro-6-allylamino-pyrimidine of m.p. 39°–40° C.

EXAMPLE 17

12.1 g (50 m-moles) of 2-ethyl-4-chloro-5-nitro-6-allylamino-pyrimidine are reacted with 50 m-moles of sodium-(2-ethylthio)-ethanolate in 100 ml of 2-ethylthio-ethanol. Yield: 7 g of 2-ethyl-4-(2'-ethylthio)-ethyloxy-5-nitro-6-allylaminopyrimidine as a yellow oil ($n_D^{20}$: 1.5680).

EXAMPLE 18

(a) 15 ml of triethylamine are added to a solution of 15.6 g of 2,4-dichloro-5-nitro-6-methylpyrimidine (0.075 mole) in 300 ml of absolute ethanol. With ice cooling, 6.6 g of sec. butylamine (0.09 mole) are added dropwise at 0°–5° C over the course of c. 40 minutes to the dark red solution. After the mixture has been stirred for c. ¾ hour at this temperature, it is poured into c. 700 ml of ice water and the water is extracted 3 times with ether. The ethereal extracts are dried over magnesium sulphate and evaporated. The resultant red oily substance is crystallised from petroleum ether to yield 10.5 g of 2-chloro-4-sec. butylamino-5-nitro-6-methyl-pyrimidine of m.p. 40°–43° C.

(b) 17.1 g of 2-chloro-4-sec. butylamino-5-nitro-6-methyl-pyrimidine (0.07 mole) are dissolved in 200 ml of methanol. To this solution is added a solution of 8.1 g of sodium methylate (0.15 mole) in 100 ml of methanol and the mixture is boiled overnight at 100° C bath temperature. After it has been cooled, the solution is evaporated and the resultant red substance is treated with ether and then filtered over Hyflo. The filter residue is washed 5 times with ether and the combined ethereal extracts are then evaporated to yield 12.3 g of 2-methoxy-4-sec. butylamino-5nitro-6-methylpyrimidine which boils at 110° C at 0.001 Torr (=73% yield).

EXAMPLE 19

12.2 g of 2-chloro-4-sec. butylamino-5-nitro-6-methylpyrimidine (0.05 mole) are dissolved in 200 ml of alcohol and 10 ml of triethylamine are added to this solution. The reaction mixture is heated to reflux temperature and then 4.5 g of methylmercaptan (0.094 mole) are passed in. Subsequently 1.2 g of sodium hydride (0.05 mole) are added at 70° C and the mixture is refluxed for 1 hour. After the reaction mixture has cooled, the sodium chloride precipitate is filtered off with suction and the filtrate is evaporated to yield 11.7 g of 2-methylthio-4-sec.butylamino-5-nitro-6-methyl-pyrimidine of m.p. 37°–41° C (= 91.5% yield). On recrystallisation from petroleum ether, the melting point of the product rises to 48°–50° C.

EXAMPLE 20

10 ml of triethylamine are added to a solution of 15.9 g of 2-chloro-4-sec. butylamino-5-nitro-6-methyl-pyrimidine (0.065 mole) in 250 ml of alcohol. Then 4.5 g (0.1 mole) of dimethylamine are passed in and the mixture is boiled for 4 hours at 100° C. After it has cooled, the mixture is evaporated and the residye is suspended in water. The resultant precipitate is filtered off with suction and washed with water until no more chlorine ions are dissolved out. The product is dried in a water jet vacuum at 50° C to yield 16.2 g of 2-dimethylamino-4-sec. butylamino-5-nitro-6-methylpyrimidine (=98.5% yield) of m.p. 98°–100° C. On recrystallisation from petroleum ether, the melting point of the product rises to 109°–110° C.

EXAMPLE 21

(a) 102.6 g of 6-isopropylurcil are added by amounts to 150 ml of 100% HNO$_3$ at 35°–40° C. The reaction mixture is stirred for ½ hour at 40° C and then poured into ice water, filtered, and the filter product is dried. Yield: 99 g of 5-nitro-6-isopropyl-uracil of m.p. 235° C.

(b) 80 ml of N,N-diethyl aniline are added dropwise to 80 g (0.4 mole) of 5-nitro-6-isopropyluracil in 400 ml of POCl$_3$ and the reaction temperature is slowly allowed to rise. The reaction mixture is refluxed overnight and then poured onto ice. The crystalline precipitate is filtered off and dried. The product is purified by adsorption chromatography on silica gel by elution with benzene. Yield: 67 g of 2,4-dichloro-5-nitro-isopropyl-pyrimidine of m.p. 43°–46° C.

(c) 20.2 g (0.2 mole) of triethylamine are added to 47.2 g (0.2 mole) of 2,4-dichloro-5-nitro-6-isopropyl-pyridine in 1 liter of ethanol and 17.5 g (0.2 mole) of 3-aminopentane are added dropwise at −20° C. The reaction mixture is stirred overnight at 20° C and then concentrated. The residue is suspended in water and extracted with ether. The ethereal extracts are drid over MgSO$_4$ and evaporated. The product is purified by adsorption chromatography on silica gel by elution with benzene to yield 48 g of 2-chloro-4-(3-pentylamino-5-nitro-6-isopropyl-pyrimidine ($n_D^{20}$: 1.5478).

(d) A solution of 14.4 g (50 m-moles) of 2-chloro-4-(3-pentylamino)-5-nitro-6-isopropyl-pyrimidine in 50 ml of ether is added dropwise to a suspension of 3.5 g (50 m-moles) of sodium methylmercaptan in 50 ml of dimethyl sulphoxide. The reaction mixture is stirred for 1 hour at 20° C, then poured into 0.5 litre of water and extracted with ether. The ethereal extracts are dried over MgSO$_4$, dried and evaporated to yield 14 g of 2-methylthio-4-(3-pentylamino)-5-nitro-6-isopropyl-pyrimidine as an oil ($n_D^{20}$: 1.5757).

EXAMPLE 22

A solution of sodium methylate in methanol (prepared from 1.2 g (50 m-moles) of sodium in 50 ml of methanol) is added to 14.4 g (50 m-moles) of 2-chloro-4-(3-pentylamino)-5-nitro-6-isopropyl-pyrimidine in 100 ml of methanol and the mixture is stirred for 1 hour. The solvent is distilled off and the residue is suspended in water and extracted with ether. The ethereal extracts are dried over MgSO$_4$ and evaporated to yield 14 g of 2-methoxy-4-(3-pentylamino)-5-nitro-6-isopropyl-pyrimidine as an oil ($n_D^{20}$: 1.5412).

EXAMPLE 23

A solution of sodium allyl alcoholate (prepared from 1.2 g (50 m-moles of sodium in 50 ml of allyl alcohol) is added to 13.2 g (50 m-moles) of 2-methylthio-4-isopropylamino-5-nitro-6-chloro-pyrimidine and the mixture is stirred overnight at 20° C. The allyl alcohol is evaporated off, the residue is suspended in water and extracted with ether. The ethereal extracts are dried over MgSO$_4$ and concentrated to yield 15 g of 2-methylthio-4-isopropylamino-5-nitro-6-allyloxypyrimidine of m.p. 51°–54° C.

The following Table lists active substances of the formula I described in the Examples as well as further ones manufactured by the processes described hereinbefore:

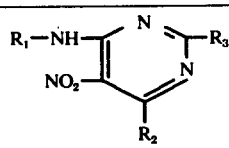

| Compound No. | R$_1$ | R$_2$ | R$_3$ | Physical Data m.p. ° C; b.p. ° C/Torr $n_D$ |
|---|---|---|---|---|
| 1 | C$_2$H$_5$ | —SC$_2$H$_5$ | CH$_3$ | mp. 98–100° |
| 2 | pentyl-(3) | —OC$_2$H$_5$ | CH$_3$ | b.p. 138°/0,001 |
| 3 | pentyl-(3) | —OC$_3$H$_7$(iso) | CH$_3$ | b.p. 115°/0,001 |
| 4 | pentyl-(3) | —SC$_3$H$_7$(iso) | CH$_3$ | b.p. 130°/0,001 |
| 5 | pentyl-(3) | —SC$_2$H$_5$ | CH$_3$ | m.p. 71–73° |
| 6 | pentyl-(3) | —SCH$_3$ | CH$_3$ | m.p. 81–82° |
| 7 | pentyl-(3) | —OCH$_3$ | CH$_3$ | b.p. 75–80°/0,001 |
| 8 | sec.-C$_4$H$_9$ | —OC$_2$H$_5$ | CH$_3$ | b.p. 75–80°/0,001 |
| 9 | pentyl-(2) | —OCH$_3$ | CH$_3$ | |
| 10 | i-C$_3$H$_7$ | —SC$_3$H$_7$(iso) | C$_2$H$_5$ | |
| 11 | i-C$_3$H$_7$ | —OC$_3$H$_7$(iso) | C$_2$H$_5$ | |
| 12 | pentyl-(3) | —SC$_2$H$_5$ | C$_2$H$_5$ | $n_D^{20}$ = 1,5738 |
| 13 | pentyl-(3) | —SCH$_3$ | C$_2$H$_5$ | $n_D^{20}$ = 1,5665 |
| 14 | pentyl-(3) | —S—C$_3$H$_7$(iso) | C$_2$H$_5$ | $n_D^{20}$ = 1,5689 |
| 15 | pentyl-(3) | —OCH$_3$ | C$_2$H$_5$ | b.p. 143°,$n_D^{20}$ = 1,5445 |
| 16 | pentyl-(3) | —OC$_2$H$_5$ | C$_2$H$_5$ | $n_D^{20}$ = 1,5308 |
| 17 | pentyl-(3) | —OC$_3$H$_7$(iso) | C$_2$H$_5$ | $n_D$ = 1,55 |
| 18 | sec.-C$_4$H$_9$ | —OC$_3$H$_7$ | —SCH$_3$ | |
| 19 | hexyl | —OCH$_3$ | C$_2$H$_5$ | |
| 20 | C$_2$H$_5$ | —S—C$_4$H$_9$(sec) | C$_2$H$_5$ | |
| 21 | C$_3$H$_7$(iso) | —SC$_3$H$_7$(iso) | CF$_3$ | |
| 22 | C$_3$H$_7$(iso) | —OC$_3$H$_7$(iso) | CF$_3$ | |
| 23 | pentyl-(3) | —SCH$_3$ | CF$_3$ | |
| 24 | pentyl-(3) | —SC$_2$H$_5$ | CF$_3$ | $n_D$ = 1,5305 |
| 25 | pentyl-(3) | —SC$_3$H$_7$(iso) | CF$_3$ | $n_D$ = 1,5260 |
| 26 | pentyl-(3) | —OCH$_3$ | CF$_3$ | |
| 27 | pentyl-(3) | —OC$_2$H$_5$ | CF$_3$ | $n_D^{20}$ = 1,4952 |
| 28 | pentyl-(3) | —OC$_3$H$_7$(iso) | CF$_3$ | |
| 29 | C$_3$H$_7$(iso) | —OC$_3$H$_7$(iso) | C$_3$H$_7$(iso) | |
| 30 | C$_2$H$_5$ | —S—C$_3$H$_7$(iso) | C$_3$H$_7$(iso) | |
| 31 | pentyl-(3) | —SCH$_3$ | C$_3$H$_7$(iso) | |
| 32 | pentyl-(3) | —SC$_2$H$_5$ | C$_3$H$_7$(iso) | $n_D^{20}$ = 1,5688 |
| 33 | pentyl-(3) | —SC$_3$H$_7$(iso) | C$_3$H$_7$(iso) | $n_D^{20}$ = 1,5600 |
| 34 | pentyl-(3) | —OCH$_3$ | C$_3$H$_7$(iso) | $n_D^{20}$ = 1,56 |
| 35 | pentyl-(3) | —OC$_2$H$_5$ | C$_3$H$_7$(iso) | m.p. 80° |
| 36 | pentyl-(3) | —OC$_3$H$_7$(iso) | C$_3$H$_7$(iso) | |
| 37 | pentyl-(3) | —SCH$_3$ | n-C$_3$H$_7$ | |
| 38 | pentyl-(3) | —SC$_2$H$_5$ | n-C$_3$H$_7$ | |
| 39 | pentyl-(3) | —SC$_3$H$_7$(iso) | n-C$_3$H$_7$ | |
| 40 | pentyl-(3) | —OCH$_3$ | n-C$_3$H$_7$ | |
| 41 | pentyl-(3) | —OC$_2$H$_5$ | n-C$_3$H$_7$ | |
| 42 | pentyl-(3) | —OC$_3$H$_7$(iso) | n-C$_3$H$_7$ | |
| 43 | C$_2$H$_5$ | —OC$_2$H$_5$ | —SCH$_3$ | m.p. 78–81° |
| 44 | C$_2$H$_5$ | —SCH$_3$ | —SCH$_3$ | m.p. 149–150° |
| 45 | pentyl-(3) | —SC$_2$H$_5$ | —SCH$_3$ | b.p. 150°/0,001 |
| 46 | pentyl-(3) | —OC$_3$H$_7$(iso) | —SCH$_3$ | b.p. 140°/0,001 |
| 47 | pentyl-(3) | —S—C$_3$H$_7$(iso) | —SCH$_3$ | b.p. 170°/0,001 |
| 48 | pentyl-(3) | —OC$_2$H$_5$ | —SCH$_3$ | b.p. 130°/0,001 |
| 49 | pentyl-(3) | —SCH$_3$ | —SCH$_3$ | |
| 50 | iso-C$_3$H$_7$ | —OCH$_3$ | —SCH$_3$ | |
| 51 | C$_2$H$_5$ | —OCH$_3$ | —OCH$_3$ | |
| 52 | C$_2$H$_5$ | 3-hexyl-S— | C$_2$H$_5$ | $n_D^{20}$ = 1,5752 |
| 53 | pentyl-3 | 2-butyl-S— | C$_2$H$_5$ | = 1,5658 |
| 54 | C$_2$H$_5$ | 2-butyl-S— | C$_2$H$_5$ | = 1,5873 |
| 55 | pentyl-3 | 3-pentyl-O— | C$_2$H$_5$ | 1,5209 |
| 56 | C$_2$H$_5$ | 3-pentyl-O— | C$_2$H$_5$ | 1,5359 |
| 57 | pentyl-3 | —SC$_3$H$_7$(n) | C$_2$H$_5$ | 1,5702 |

-continued

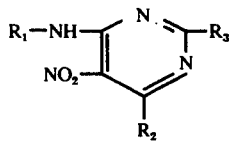

| Compound No. | R₁ | R₂ | R₃ | Physical Data m.p. ° C; b.p. ° C/Torr $n_D$ |
|---|---|---|---|---|
| 58 | pentyl-3 | —OC₃H₇(n) | C₂H₅ | 1,5308 |
| 59 | pentyl-3 | —OC₂H₅ | OC₂H₅ | m.p. 40° C |
| 60 | pentyl-3 | —OC₃H₇ | SCH₃ | b.p. 135–140/0,001 |
| 61 | pentyl-3 | —OC₃H₇ | CH₃ | b.p. 130°/0,001 |
| 62 | pentyl-3 | —OC₂H₅ | C₄H₉(n) | $n_D^{20}$ 1,5310 |
| 63 | i-C₃H₇ | cyclohexyl-S— | C₂H₅ | m.p.: 69–71° C |
| 64 | i-C₃H₇ | —OC₂H₅ | C₂H₅ | m.p.: 34–35° |
| 65 | cyclo-C₃H₅ | —OC₂H₅ | C₂H₅ | m.p.: 79–80° |
| 66 | CH₂=CH—CH₂— | —O—C₂H₅ | C₂H₅ | m.p.: 33–35° |
| 67 | i-C₃H₇ | —S—C₂H₅ | C₂H₅ | $n_D^{20}$: 1,5880 |
| 68 | cyclo-C₃H₅ | —S—C₂H₅ | C₂H₅ | m.p.: 73–74° |
| 69 | CH₂=CH—CH₂— | —S—C₂H₅ | C₂H₅ | m.p.: 39–40° |
| 70 | cyclo-C₃H₅ | —O—C₂H₅ | CH₃ | |
| 71 | cyclo-C₃H₅ | —SC₂H₅ | CH₃ | |
| 72 | (CH₃)₂CH— | CH₂=CH—CH₂—S— | —SCH₃ | $n_D^{20}$: 1,6420 |
| 73 | (CH₃)₂CH— | CH₂=CH—CH₂—O— | —SCH₃ | m.p.: 51–54° |
| 74 | (CH₃)₂CH— | CH₂=CH—CH₂—S— | C₂H₅ | $n_D^{20}$: 1,5945 |
| 75 | (CH₃)₂—CH— | CH₂=CH—CH₂—O— | C₂H₅ | $n_D^{20}$: 1,5449 |
| 76 | pentyl-3 | cyclopropyl-O— | CH₃ | |
| 77 | (CH₃)₂CH— | cyclopropyl-O | C₂H₅ | $n_D^{20}$: 1,5432 |
| 78 | pentyl-3 | cyclopropyl-S— | CH₃ | |
| 79 | pentyl-3 | cyclopropyl-CH₂— | CH₃ | |
| 80 | cyclo-C₃H₅— | CH₃—O—CH₂—CH₂O | C₂H₅ | $n_D^{20}$: 1,5572 |
| 81 | CH₂=CH—CH₂— | C₂H₅—S—CH₂—CH₂-O— | C₂H₅— | $n_D^{20}$: 1,5680 |
| 82 | pentyl-3- | CH₃—O—CH₂CH₂—S— | CH₃ | |
| 83 | pentyl-3- | Cl—CH₂CH₂—O— | CH₃ | |
| 84 | (CH₃—CH(CH₃))₂CH— | C₂H₅—O | CH₃ | |
| 85 | C₄H₉—CH(CH₃)— | C₂H₅—S | C₂H₅ | |
| 86 | i-C₃H₇ | —S—C₃H₇(iso) | H | |
| 87 | C₂H₅ | —SC₃H₇(iso) | H | |
| 88 | C₂H₅ | —OC₃H₇(iso) | H | |
| 89 | pentyl-3 | SC₂H₅ | H | |
| 90 | sec.C₄H₉ | —OCH₃ | H | b.p. 104°/0,001 |
| 91 | C₂H₅ | n—C₃H₇ | SCH₃ | |
| 92 | pentyl-3 | C₂H₅ | SCH₃ | |
| 93 | pentyl-3 | i-C₃H₇ | —OCH₃ | |
| 94 | pentyl-3 | i-C₃H₇ | —SCH₃ | |
| 95 | pentyl-3 | n-C₃H₇ | —OCH₃ | $n_D^{20}$: 1,5412 |
| 96 | pentyl-3 | n-C₄H₉ | —S—CH₃ | |
| 97 | pentyl-3 | n-C₃H₇ | —SCH₃ | $n_D^{20}$: 1,5757 |

New intermediate products of the formulae IIa to IIc which can be used for the manufacture of the end products listed in the previous Table and of further end products are listed hereinbelow.

| Intermediate No. | R₁ | R₂ | R₃ | Physical Data m.p. °C;b.p. °C/Torr $n_D^{b}$ |
|---|---|---|---|---|
| 1 | C₃H₇(iso) | Cl | CH₃ | m.p. 77–79° |
| 2 | C₂H₅ | Cl | CH₃ | m.p. 61–63° |
| 3 | pentyl-(3) | Cl | CH₃ | m.p. 42–44° |
| 4 | C₃H₇(iso) | Cl | C₂H₅ | m.p. 55° |
| 5 | pentyl-(3) | Cl | C₂H₅ | $n_D^{20} = 1,5465$ |
| 6 | C₂H₅ | Cl | CF₃ | |
| 7 | pentyl-(3) | Cl | CF₃ | $n_D^{20} = 1,5014$ |
| 8 | pentyl-(3) | Cl | iso-C₃H₇ | $n_D^{20} = 1,5382$ |
| 9 | pentyl-(3) | Cl | n-C₃H₇ | |
| 10 | C₂H₅ | Cl | —SCH₃ | m.p. 100–101° |
| 11 | pentyl-(3) | n-C₃H₇ | Cl | $n_D^{20} = 1,5478$ |
| 12 | C₂H₅ | Cl | —N(CH₃)₂ | |
| 13 | C₂H₅ | Cl | H | m.p. 114° |
| 14 | sec. C₄H₉ | Cl | H | b.p. 87/0,001 |
| 15 | C₆H₁₃ | Cl | H | m.p. 25–27° |
| 16 | cyclopentyl | Cl | H | m.p. 60° |
| 17 | iso-C₃H₇ | Cl | H | m.p. 72–74° |
| 18 | C₂H₅ | Cl | H | m.p. 120–122° |
| 19 | sec. C₄H₉ | Cl | H | b.p. 87°/0,001 |
| 20 | cyclo-propyl | Cl | C₂H₅ | |
| 21 | CH₂=CH—CH₂— | Cl | C₂H₅ | |
| 22 | cyclo-propyl | Cl | CH₃ | |
| 23 | C₂H₅ | Cl | C₂H₅ | m.p. 40–42° |

The active substances of the formula I are soluble and stable in organic solvents. Some have a slight tendency to undergo hydrolysis in water.

As already mentioned, these active substances can be used as herbicides and plant growth regulators. A number of them even effect growth inhibition in soya plantations, which results in marked increases in yield.

Some of the active substances when used as selective preemergent herbicides effect as very good selectivity in wheat, barley, soya, cotton, lucernes and ground nuts. The active substances can be used as post-emergent herbicides in cereals, in which connection some of them even have an outstanding action against Avena fatua (wild oats).

The active substances have an insignificant toxicity and in rats the $DL_{50}$ p.o. is above 1000 mg/kg.

PROOF OF ACTIVITY (a) Preemergent herbicidal action:

Immediately after the test plants have been sown in seed dishes, the active substances are applied as an aqueous suspension, obtained from a 25% wettable powder, to the surface of the soil in concentration of 1 kg/ha. The seed dishes are kept at 22°–23° C and 50 to 70% relative humidity. The test is evaluated after 28 days. The test plants used are:

weeds:
*Digitaria sanguanalis*
*Amaranthus retroflexus*
*Lolium perenne*
*Rottboellia ex.*
*Ipomoea purp.*
*Galium aparine*

Crop plants:
soya (*Glycine hyspida*)
cotton (*Gossypium herbaccara*)
maize (*Zea Mais*)
wheat (triticum vulgare)

The evaluation is made according to the following rating:

1 = plants withered
2—8 = intermediate stages of damage
9 = plants undamaged (control)

In this test the active substances according to the invention showed evidence of excellent herbicidal action against the indicated test weeds. Compared with 2-methylthio-5-nitro-4-(pentyl)-(3)-amino)-6-alkylaminopyrimidines of DOS 2,223,644, the results show a better action agains weeds with just as little damage to most of the crop plants:

Results

| Compound No. | Triticum (wheat) | Zea (maize) | Glycine (soya) | Gossypium (cotton) | Lolium perenne | Rottboellia exalt. | Digitaria Sang. | Amaranthus r. | Ipomoea purp. | Galium apar. |
|---|---|---|---|---|---|---|---|---|---|---|
| according to the invention | | | | | | | | | | |
| 45 | 9 | 9 | 9 | 9 | 2 | 3 | 1 | 3 | 7 | 9 |
| 46 | 8 | 8 | 9 | 9 | 4 | 2 | 1 | 1 | 6 | 9 |
| 47 | 9 | 9 | 9 | 8 | 2 | 3 | 2 | 2 | 9 | 8 |
| 2 | 8 | 2 | 8 | 8 | 2 | 2 | 1 | 1 | 3 | 8 |
| 48 | 9 | 9 | 9 | 9 | 9 | 5 | 1 | 1 | 6 | 1 |
| 15 | 9 | 9 | 9 | 9 | 9 | 1 | 1 | 3 | 9 | 9 |
| 24 | 9 | 9 | 9 | 9 | 2 | 1 | 1 | 1 | 4 | 9 |
| Comparison | | | | | | | | | | |
| I | 8 | 8 | 9 | 9 | 5 | 3 | 1 | 2 | 8 | 6 |
| II | 8 | 7 | 8 | 9 | 4 | 2 | 1 | 3 | 6 | 9 |

I = 2-methylthio-6-ethylamino-5-nitro-4-pentyl-(3)-amino-pyrimidine
II = 2-methylthio-6-isopropylamino-5-nitro-4-pentyl-(3)-amino-pyrimidine.

Each of the tested compounds 1 to 4 according to the invention is more effective than the 2 known comparison substances of DOS 2,223,644 while causing virtually as little damage to the crop plants. Compound 48 is exceptionally suited to combating the problem weed Galium.

(b) Post-emergent herbicidal action

Avena sativa, Lolium perenne, Sinapis alba and Stellaria media are sprayed in the 4 to 6 leaf stage with an aqueous active substance emulsion in a rate of application of 4 kg/ha. The plants are then kept at 24°–26° C and 45–60% relative humidity. The test is evaluated 14 days after treatment. Evaluation as in (a).

Results

| Compound No. | Avena sativa | Lolium perenne | Sinapis alba | Stellaria media |
|---|---|---|---|---|
| 14 | 3 | 6 | 3 | 3 |
| 16 | 2 | 3 | 1 | 2 |
| 57 | 4 | 5 | 2 | 2 |
| 58 | 2 | 5 | 1 | 2 |
| 60 | 3 | 4 | 3 | 3 |
| I | 5 | 5 | 4 | 3 |
| II | 4 | 4 | 4 | 4 |

On average, the active substances according to the invention have a better post-herbicidal action than the principal products I and II of DOS 2,223,644.

(c) Sucker control in tobacco plants

Tobacco plants of the variety "Canthi" reared in a greenhouse were cut back (tips of the side-shoots snipped off) shortly before blossoming. Five days later, when the suckers growing from the leaf axils averaged 2 cm in length, 6 plants at a time were sprayed with aqueous preparations of the active substances. The rates of application corresponded to 12.6 and 3 kg respectively of active substance per hectare. Cut back, untreted plants were used in the test as controls. The test was evaluated 14 days after application by determining the number of withered suckers and by measuring the length of the remaining suckers. The following results were obtained.:

| treatment | withered suckers in % | average new growth of the remaining suckers after the application in % |
|---|---|---|
| Control | 0% | 100% (16,3 cm) |
| Compound No. 46 | | |
| 12 kgAS/ha | 37% | 6% (0,9 cm) |
| 6 kgAS/ha | 16% | 11% (1,8 cm) |
| 3 kgAS/ha | 5% | 13% (2,2 cm) |
| Compound No. 12 | | |
| 12 kg AS/ha | 91% | 7% (1,1 cm) |
| 6 kg AS/ha | 76% | 10% (1,6 cm) |
| 3 kg AS/ha | 40% | 10% (1,6 cm) |

On account of the pronounced sucker inhibition (i.e. suppression of competition in the nutrient consuptin), the upper leaves of the plants treated with active substances 12 and 46 of the Table were far better developed than those of the control plants.

The agents according to the invention are manufactured in known manner by intimately mixing and/or grinding active substances of the formula I with the suitable carriers, optionally with the addition of dispersants or solvents which are inert towards the active substances. The active substances may take and be used in the following forms:

Solid forms:
dusts, tracking agents, granules, coated granules, impregnated granules and homogeneous granules.
Liquid forms:
(a) active substances which are dispersible in water: wettable powders, pastes, emulsions;
(b) solutions.

Solid forms (dusts, tracking agents), are manufactured by mixing the active substances with soled carriers. Suitable carriers are, for example: kaolin, talcum, bolus, loess, chalk, limestone, ground limestone, attaclay, dolomite, diatomacous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder residues of plant extractions, activated charcoal etc. These substances can either be used singly or in admixture with one another.

The particle size of the carriers for dusts is advantageously up to 0.1 mm, for tracking agents from about 0.075 to 0.2 mm, and for granules 0.2 mm or larger.

The solid forms contain the active substances in concentrations from 0.5 to 80%.

To these mixtures can also be added additives which stabilize the active substance and/or non-ionic, anionic and cationic surface active substances, which for example improve the adhesion of the active ingredients on plants or parts of plants (adhesives and agglutinants) and/or ensure a better wettability (wetting agents) and dispersibility (dispersing agents). Examples of suitable adhesives are: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, the alkali metal and alkaline earth metal salts thereof, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of urea and formaldehyde, and also latex products.

The water-dispersible concentrates of the active substance i.e. wettable powders, pastes and emulsifiable concentrates, are agents which can be diluted with water to any concentration desired. They consist of active substance, carrier, optionally additives which stabilize the active substance, surface-active substances and anti-foam agents and, optionally, solvents. The active substance concentrations in these agents are from 5 – 80%.

Wettable powders and pastes are obtained by mixing and grinding the active substances with dispersing agents and pulverulent carriers in suitable devices until homogeneity is attained. Carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphates fatty alcohol gylcol ethers, the sodium salt of oleyl methyl tauride, ditertiary acetalene glycols, dialkyl dilauryl ammonium chloride and fatty acid alkali and alkaline earth metal salts.

Suitable anti-foam agents are silicones.

The active substance is so mixed, ground sieved and strained with the additives mentioned above that, in wettable powders, the solid particle size of 0.02 to 0.04 mm and in pasts, of 0.03 mm is not exceeded. Emulsion concentrates and pastes are manufactured by using dispersing agents, such as those cited in the previous paragraphs, organic solvents and water. Examples of suitable solvents are: alcohols, benzene, xylenes, toluene, dimethyl sulphoxide, and mineral oil fractions which boil between 120° and 350° C. The solvents must be practically odorless, not phytotoxic, inert to the active substances and not readily inflammable.

Furthermore, the agents according to the invention can be applied in the form of solutions. For this purpose the active substances or several active substances of general formula II are dissolved in suitable organic solvents, mixtures of solvents or in water. Aliphatic and aromatic hydrocarbons, chlorinted derivatives thereof, alkyl naphthalenes and mineral oils singly or in admixture, can be used as organic solvents. The solutions contain the active substance in a concentration range from 1 to 20 %. These solutions can be applied either with a propellant gas (as spray) or with special sprays (as aerosol). The agents described according to the invention can be mixed with other biocidally active substances or agents. Thus in order to broaden the activity spectrum the new agents may contain, for example, inceticided, fungicides, bactericides, fungistats, bacteriostats or nematocides, in addition to the cited active substance of the formula I. The agents according to the invention may also contain plant fertilisers, trace elements etc.

Formulations of the new active substances of the formula I are described hereinafter. Parts denote parts by weight.

Granules

The following substances are used to manufacture 5% granules:
5 parts of 2-methylthio-6-ethoxy-5-nitro-4-ethylamino-pyrimidine
0.25 parts of epichlorohydrin,
0.25 parts of cetyl polyglacol ether,
3.50 parts of polyethylene glycol,
91 parts of kaolin (particle size 0.3 —0.8 mm).

The active substance is mixed with epichlorohydrin and dissolved with 6 parts of acetone; the polyethylene glycol and cetyl polyglycol ether are then added. The resultant solution is sprayed on kaolin and the acetone subsequently evaporated in vacuo.

Wettable Powder

The following constituents are used to manufacture (a) a 50 %, (b) a 25 % and (c) a 10 % wettable powder:
(a)
50 parts of 2-methylthio-6ethylthio-5-nitro-4-(pentyl-(3)-amino)-pyrimidine,
5 parts of sodium dibutylnaphthalene sulphate,
3 parts of naphthalenesulphonic acid/phenolsulphonic acid/formaldehyde condensate (3:2:1),
20 parts of kaolin,
22 parts of Champagne chalk;
(b)
25 parts of 2-methoxy-6-methyl-5-nitro-4-sec.-butylamino-pyrimidine 5 parts of sodium oleylmethyltauride,
2.5 parts of naphthalenesulphonic acid/formaldehyde condensate,
0.5 part of carboxymethyl cellulose,
5 parts of neutral potassium aluminium silicate,
62 parts of kaolin;
(c)
10 parts of 2-methyl-4-pentyl-(3)-amino-5-nitro-6-ethoxy-pyrimidine,
3 parts of a mixture of the sodium salts of saturated fatty alcohol sulphates,
5 parts of naphthalenesulphonic acid/formaldehyde condensate
82 parts of kaolin.

The respective active substance is applied to the corresponding carriers (kaolin and chalk) and then these are mixed and ground, to yield wettable powders of excellent wettability and suspension power. By diluting these wettable powders with water it is possible to obtain suspensions of every desired concentration of active substance. Such suspensions are used for combating weeds and grass-like weeds in food crops in the preemergence method and for treating grass crops.

Paste

The following substances are used to manufacture a 45 % paste:
45 parts of 2-methyl- or 2-methylthio-4-[pentyl-(3')-amino]-5-nitro-6-isopropylthio-pyrimidine,
5 parts of sodium aluminium silicate,
14 parts of cetyl polyglycol ether with 8 mols of ethylene oxide,
1 part of oleyl polyglycol ether with 5 mols of ethylene oxide,
2 parts of spindle oil,
10 parts of polyethylene glycol,
23 parts of water.

The active substance is intimately mixed with the additives in appropriate devices and ground. A paste is obtained from which, by dilution with water, it is possible to manufacture suspensions of every desired concentration of active substance. The suspensions are suitable for treating grass lawns.

Emulsion Concentrate

The following ingredients are mixed to manufacture a 25 % emulsion concentrate:
25 parts of 2-methyl- or 2-methylthio-4-[pentyl-(3')-amino]-5-nitro-6-isopropoxy-pyrimidine,
5 parts of a mixture of nonylphenolpolyoxy-ethoxyethylene and calcium dodecylenesulphonate,
35 parts of 3,5,5-trimethyl-2-cyclohexan-1-one,
35 parts of dimethyl formamide.

This concentrate can be diluted with water to give emulsions in desired concentrations. Such emulsions are suitable for combating weeds in food crops.

Instead of the respective active substance used in the preceding formulations, it is also possible to use another of the compounds comprises by the formula I.

I claim:
1. A 5-nitro-pyrimidine derivative of the formula I

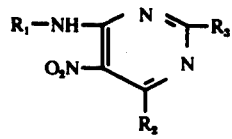

(I)

wherein $R_1$ represents an alkyl radical of 2 to 7 carbon atoms, an alkenyl radical of 3 to 5 carbon atoms, or a cycloalkyl radical of 3 to 6 carbon atoms, $R_2$ represents an alkyl radical of 2 to 6 carbon atoms, an alkoxy or an alkylthio radical of 1 to 6 carbon atoms, an alkenyloxy or alkenylthio radical of 2 to 4 carbon atoms, a cyloalkoxy or cycloalkylthio radical of 3 to 6 carbon atoms, $R_3$ represents hydrogen, an alkyl, haloalkyl, alkoxy or alkylthio radical of 1 to 4 carbon atoms or a di-($C_1$-$C_4$-alkyl)-amino radical, and the addition salts thereof with inorganic or organic acids selected from the group consisting of hydrochloric acid, hydrobromic acid, phosphoric acid, sulfuric acid, nitric acid, fluoroboric acid, perchloric acid, methyl sulfuric acid, ethylsulfuric acid, halobenzoic acids, trichloroacetic acid, methane sulphonic acid and p-toluene sulfonic acid.

2. 5-nitro-pyrimidine derivative of the formula I acording to claim 1, wherein $R_1$ represents a branched alkyl radical of 2 to 5 carbon atoms or the cyclopropyl radical, $R_2$ represents an alkyl radical of 3 to 4 carbon atoms, an alkoxy or alkylthio radical of 1 to 6 carbon atoms, the allyloxy or allylthio radical, and $R_3$ represents an alkyl radical of 1 to 4 carbon atoms, an alkoxy or alkylthio radical of 1 to 4 carbon atoms or represents the $CF_3$ group.

3. 5-nitro-pyrimidine derivative of the formula I according to claims 2, wherein $R_1$ represents the radical —$CH(C_2H_5)_2$, $R_2$ represents an alkoxy or alkylthio radical of 1 to 4 carbon atoms and $R_3$ represents the methyl, ethyl, methylthio or $CF_3$ group.

4. A composition for influencing plant growth, which comprises as active substance an effective amount of a 5-nitropyrimidine derivative of the formula I of claim 1, or a salt of such a compound, together with a suitable carrier therefor.

5. A method of influencing plant growth which commprises treating crop plants before or after the emergence of the plants with an effective amount of a compound according to claim 1.

6. The method according to claim 5 which comprises treating emergent plants in order to regulate their growth.

7. The method according to claim 6 for regulating the growth in height of grasses and cereals.

8. The method according to claim 6 for inhibiting the growth of suckers in tobacco plants.

* * * * *